US00RE34584E

United States Patent [19]

Grote et al.

[11] E Patent Number: Re. 34,584

[45] Reissued Date of Patent: Apr. 12, 1994

[54] SHAMPOO COMPOSITIONS

[75] Inventors: Mark B. Grote, Cincinnati; Glen D. Russell, Loveland, both of Ohio

[73] Assignee: The Procter & Gamble Company, Cincinnati, Ohio

[21] Appl. No.: 517,111

[22] Filed: May 1, 1990

Related U.S. Patent Documents

Reissue of:

[64] Patent No.: 4,741,855
Issued: May 3, 1988
Appl. No.: 80,022
Filed: May 3, 1988

U.S. Applications:

[63] Continuation of Ser. No. 795,285, Nov. 5, 1985, abandoned, which is a continuation-in-part of Ser. No. 670,189, Nov. 9, 1984, abandoned.

[51] Int. Cl.[5] ..... A61K 7/075; C11D 3/20; C11D 9/36; C11D 17/08

[52] U.S. Cl. ..... 252/142; 252/89.1; 252/173; 252/174.15; 252/312; 252/546; 252/547; 252/548; 252/DIG. 13; 424/70; 424/73

[58] Field of Search ..... 252/DIG. 13, 89.1, 142, 252/174.15, 312, 546, 547, 548, DIG. 5, 173; 424/70, 73

[56] References Cited

U.S. PATENT DOCUMENTS

| | | | |
|---|---|---|---|
| 2,406,671 | 8/1946 | Diamond | 252/49.6 |
| 2,523,281 | 9/1950 | Currie | 106/3 |
| 2,584,413 | 2/1952 | Baer et al. | 106/11 |
| 2,586,211 | 2/1952 | Currie | 18/47 |
| 2,595,928 | 5/1952 | Currie et al. | 252/358 |
| 2,666,685 | 1/1954 | Hommel et al. | 106/38.22 |
| 2,702,276 | 2/1955 | Green | 252/8.6 |
| 2,755,194 | 7/1956 | Volkmann et al. | 106/285 |
| 2,757,094 | 7/1956 | Guss | 106/8 |
| 2,757,152 | 7/1956 | Solomon | 260/29.2 |
| 2,799,599 | 7/1957 | Koch | 117/141 |
| 2,803,614 | 8/1957 | Solomon | 260/29.4 |
| 2,826,551 | 3/1958 | Geen . | |
| 2,829,112 | 4/1958 | Solomon | 252/358 |
| 2,833,658 | 5/1958 | May | 106/38.24 |
| 2,891,920 | 6/1959 | Hyde et al. | 260/29.2 |
| 2,955,047 | 10/1960 | Terry | 106/3 |
| 2,957,839 | 10/1960 | Johnson et al. | 260/29.2 |
| 3,113,930 | 12/1963 | Chevalier | 252/358 |
| 3,136,696 | 6/1964 | Harrison | 167/85 |
| 3,140,198 | 7/1964 | Dawson et al. | 117/138.8 |

(List continued on next page.)

FOREIGN PATENT DOCUMENTS

| | | |
|---|---|---|
| 1261276 | 9/1989 | Canada . |
| 103450 | 1/1966 | Denmark . |
| 35899 | 9/1981 | European Pat. Off. . |
| 57837 | 8/1982 | European Pat. Off. . |

(List continued on next page.)

OTHER PUBLICATIONS

Bennett, H., Editor, 1974, *Chemical Formulary*, vol. XVIII, p. 167.

Ash et al., 1980, *A Formulary of Detergents and Other Cleansing Agents*, p. 76.

(List continued on next page.)

*Primary Examiner*—Linda Skaling
*Attorney, Agent, or Firm*—Steven J. Goldstein

[57] ABSTRACT

Shampoos are disclosed which comprise a synthetic surfactant, an insoluble, non-volatile silicone, a suspending agent and water. Suitable suspending agents include long chain esters of ethylene glycol, esters of long chain fatty acids, long chain amine oxides among many others.

20 Claims, No Drawings

U.S. PATENT DOCUMENTS

| | | | |
|---|---|---|---|
| 3,185,627 | 5/1965 | Kass | 167/90 |
| 3,200,080 | 8/1965 | Martin et al. | 252/358 |
| 3,210,208 | 10/1965 | Grass et al. | 106/148 |
| 3,235,509 | 2/1966 | Nitzsche et al. | 252/358 |
| 3,294,709 | 12/1966 | Nitzsche et al. | 260/23 |
| 3,336,231 | 8/1967 | Marsh et al. | 252/152 |
| 3,382,150 | 5/1968 | Grass et al. | 167/82 |
| 3,393,078 | 7/1968 | Lockhart et al. | 106/8 |
| 3,395,028 | 7/1968 | Mackles | 106/8 |
| 3,423,340 | 1/1969 | Marshall et al. | 260/13 |
| 3,433,780 | 3/1969 | Cekada et al. | 260/29.2 |
| 3,488,217 | 1/1970 | Ryan | 117/138.8 |
| 3,510,433 | 5/1970 | Pasowicz | 252/180 |
| 3,544,498 | 12/1970 | Holdstock et al. | 260/29.2 |
| 3,634,285 | 1/1972 | Brooks | 252/312 |
| 3,650,979 | 3/1972 | Steinbach et al. | 252/358 |
| 3,653,955 | 4/1972 | Habib | 117/139.5 |
| 3,655,865 | 4/1972 | Murphy | 424/45 |
| 3,691,091 | 9/1972 | Koerner | 252/358 |
| 3,755,560 | 8/1973 | Dickert et al. | 424/78 |
| 3,795,538 | 3/1974 | Evans et al. | 117/139.5 |
| 3,836,647 | 9/1974 | Lange | 424/184 |
| 3,847,622 | 11/1974 | Brandl et al. | 106/10 |
| 3,849,348 | 11/1974 | Hewitt | 252/547 |
| 3,852,075 | 12/1974 | Basadur | 106/11 |
| 3,872,038 | 3/1975 | Adams et al. | 260/13 |
| 3,925,242 | 12/1975 | Sagi et al. | 252/321 |
| 3,929,492 | 12/1975 | Chapman et al. | 106/3 |
| 3,931,079 | 1/1976 | Wise et al. | 260/28.5 |
| 3,950,510 | 4/1976 | Adams | 424/70 |
| 3,957,970 | 5/1976 | Korkis | 424/70 |
| 3,964,500 | 6/1976 | Drakoff | 132/7 |
| 3,965,518 | 6/1976 | Muoio | 15/104 |
| 3,975,294 | 8/1976 | Dumoulin | 252/354 |
| 3,980,617 | 9/1976 | Jacquet et al. | 260/47 |
| 4,005,044 | 1/1977 | Raleigh | 252/358 |
| 4,012,334 | 3/1977 | Raleigh | 252/321 |
| 4,013,475 | 3/1977 | Liebowitz et al. | 106/10 |
| 4,020,199 | 4/1977 | Nomura et al. | 427/334 |
| 4,032,473 | 6/1977 | Berg et al. | 252/358 |
| 4,039,469 | 8/1977 | Raleigh | 252/358 |
| 4,054,670 | 10/1977 | Buhler | 424/358 |
| 4,061,585 | 12/1977 | Finn et al. | 252/89 R |
| 4,071,468 | 1/1978 | Abel et al. | 252/321 |
| 4,075,118 | 2/1978 | Gault et al. | 252/135 |
| 4,080,310 | 3/1978 | Ng et al. | 252/544 |
| 4,089,882 | 7/1978 | Lang et al. | 424/59 |
| 4,113,677 | 9/1978 | Svedas et al. | 260/23 |
| 4,118,235 | 10/1978 | Horiuchi et al. | 106/38 |
| 4,118,423 | 10/1978 | Vanlerberghe et al. | 260/584 |
| 4,151,301 | 4/1979 | Kalopissis | 424/316 |
| 4,177,177 | 12/1979 | Vanderhoff et al. | 260/29.2 |
| 4,179,426 | 12/1979 | Steinbach et al. | 260/29.2 |
| 4,183,917 | 1/1980 | Iwao et al. | 424/70 |
| 4,185,087 | 1/1980 | Morlino | 424/70 |
| 4,194,988 | 3/1980 | Schneider et al. | 252/312 |
| 4,208,301 | 6/1980 | Gammon | 252/321 |
| 4,218,250 | 8/1980 | Kasprzak | 106/3 |
| 4,225,456 | 9/1980 | Schmidt et al. | 252/321 |
| 4,229,479 | 10/1980 | Brickl et al. | 424/331 |
| 4,244,742 | 1/1981 | Huber et al. | 106/38.22 |
| 4,244,948 | 1/1981 | Boghosian et al. | 424/230 |
| 4,246,029 | 1/1981 | Sanders et al. | 106/3 |
| 4,254,104 | 3/1981 | Suzuki | 424/170 |
| 4,269,739 | 5/1981 | Grejaner | 252/547 |
| 4,272,519 | 6/1981 | Herrold et al. | 424/83 |
| 4,273,584 | 6/1981 | D'Angelo et al. | 106/3 |
| 4,274,977 | 6/1981 | Koerner et al. | 252/358 |
| 4,275,222 | 6/1981 | Scala, Jr. | 560/103 |
| 4,278,657 | 7/1981 | Tezuka et al. | 424/63 |
| 4,281,201 | 7/1981 | Abend | 564/506 |
| 4,288,356 | 9/1981 | Huebner et al. | 260/29.2 |
| 4,302,364 | 11/1981 | Gosset et al. | 252/545 |
| 4,333,862 | 6/1982 | Smith et al. | 252/547 |
| 4,337,166 | 6/1982 | Hill et al. | 252/174.15 |
| 4,338,375 | 7/1982 | Hashimoto et al. | 428/412 |
| 4,341,799 | 7/1982 | Good | 424/365 |
| 4,342,742 | 8/1982 | Sebag et al. | 424/59 |
| 4,345,080 | 8/1982 | Bolich | 546/6 |
| 4,364,837 | 12/1982 | Pader | 252/173 |
| 4,383,062 | 5/1983 | Saad et al. | 524/35 |
| 4,388,437 | 6/1983 | Ona | 524/588 |
| 4,390,451 | 6/1983 | Havinga et al. | 252/311 |
| 4,391,765 | 7/1983 | Lee et al. | 264/26 |
| 4,395,352 | 7/1983 | Kulkarni et al. | 252/321 |
| 4,405,490 | 9/1983 | Maas et al. | 252/358 |
| 4,412,943 | 11/1983 | Hirota et al. | 252/546 |
| 4,421,656 | 12/1983 | Donatelli et al. | 252/8.5 P |
| 4,421,769 | 12/1983 | Dixon et al. | 424/358 |
| 4,423,041 | 12/1983 | Clum et al. | 424/184 |
| 4,425,364 | 1/1984 | Vanlerberghe et al. | 424/358 |
| 4,433,013 | 2/1984 | Puhringer | 427/337 |
| 4,439,342 | 3/1984 | Albanese | 252/305 |
| 4,443,359 | 4/1984 | Shimizu et al. | 252/358 |
| 4,452,732 | 6/1984 | Bolich, Jr. | 252/547 |
| 4,465,619 | 8/1984 | Boskamp | 252/540 |
| 4,470,982 | 9/1984 | Winkler | 424/245 |
| 4,473,667 | 9/1984 | Sands | 521/122 |
| 4,476,282 | 10/1984 | Koerner et al. | 524/837 |
| 4,479,893 | 10/1984 | Hirota et al. | 252/542 |
| 4,497,919 | 2/1985 | Varga et al. | 524/10 |
| 4,501,619 | 2/1985 | Gee | 106/287.12 |

(List continued on next page.)

U.S. PATENT DOCUMENTS

| | | | |
|---|---|---|---|
| 4,509,981 | 4/1985 | Sanders, Jr. et al. | 106/3 |
| 4,509,984 | 4/1985 | Scheiderich et al. | 106/38.22 |
| 4,511,489 | 4/1985 | Requejo et al. | 252/172 |
| 4,518,727 | 5/1985 | Traver | 524/35 |
| 4,522,808 | 6/1985 | Jacquet et al. | 424/59 |
| 4,524,172 | 6/1985 | Steinberger et al. | 524/506 |
| 4,525,502 | 6/1985 | Traver | 524/96 |
| 4,529,586 | 7/1985 | DeMarco et al. | 424/70 |
| 4,529,758 | 7/1985 | Traver | 524/43 |
| 4,534,981 | 8/1985 | Zabotto et al. | 514/783 |
| 4,541,936 | 9/1985 | Ona et al. | 252/8.6 |
| 4,559,162 | 12/1985 | Abel et al. | 252/321 |
| 4,559,227 | 12/1985 | Chandra | 424/70 |
| 4,567,038 | 1/1986 | Ciaudelli et al. | 424/59 |
| 4,582,874 | 4/1986 | Grape et al. | 524/588 |
| 4,584,125 | 4/1986 | Griswold et al. | 252/358 |
| 4,590,069 | 5/1986 | Deckner et al. | 424/70 |
| 4,597,962 | 7/1986 | Grollier et al. | 424/70 |
| 4,600,436 | 7/1986 | Traver et al. | 106/3 |
| 4,601,902 | 7/1986 | Fridd et al. | 424/70 |
| 4,609,750 | 9/1986 | Kollmeier et al. | 556/419 |
| 4,613,646 | 9/1986 | Sandvick | 524/476 |
| 4,620,878 | 11/1986 | Gee | 106/287 |
| 4,639,489 | 1/1987 | Aizawa et al. | 524/588 |
| 4,648,904 | 3/1987 | DePasquale et al. | 106/2 |
| 4,654,161 | 3/1987 | Kollmeier et al. | 252/174.15 |
| 4,658,839 | 4/1987 | Dallal et al. | 132/7 |
| 4,663,157 | 5/1987 | Brock | 424/59 |
| 4,673,568 | 6/1987 | Grollier et al. | 424/47 |
| 4,675,125 | 6/1987 | Sturwold | 252/118 |
| 4,675,179 | 6/1987 | Suzuki et al. | 424/67 |
| 4,678,815 | 7/1987 | Hoffman | 523/122 |
| 4,689,168 | 8/1987 | Requejo | 252/139 |
| 4,698,178 | 10/1987 | Huttinger et al. | 252/309 |
| 4,704,272 | 11/1987 | Oh et al. | 424/70 |
| 4,710,314 | 12/1987 | Madrange et al. | 252/117 |
| 4,728,457 | 3/1988 | Fieler | 252/174 |
| 4,732,612 | 3/1988 | Steer et al. | 106/10 |
| 4,782,095 | 11/1988 | Gum | 514/937 |
| 4,788,001 | 11/1988 | Narula | 252/312 |
| 4,788,006 | 11/1988 | Bolich, Jr. et al. | 252/550 |
| 4,801,447 | 1/1989 | Gum | 424/68 |
| 4,820,308 | 4/1989 | Madrange et al. | 8/405 |
| 4,842,849 | 6/1989 | Grollier et al. | 424/70 |
| 4,874,547 | 10/1989 | Narula | 252/312 |

FOREIGN PATENT DOCUMENTS

| | | |
|---|---|---|
| 95238 | 11/1983 | European Pat. Off. . |
| 77920 | 5/1984 | European Pat. Off. . |
| 108517 | 5/1984 | European Pat. Off. . |
| 141593 | 5/1985 | European Pat. Off. . |
| 0152194 | 6/1985 | European Pat. Off. . |
| 152194 | 8/1985 | European Pat. Off. . |
| 155806 | 9/1985 | European Pat. Off. . |
| 166232 | 1/1986 | European Pat. Off. . |
| 180464 | 5/1986 | European Pat. Off. . |
| 181773A2 | 5/1988 | European Pat. Off. . |
| 285388A2 | 10/1988 | European Pat. Off. . |
| 412705A2 | 2/1991 | European Pat. Off. . |
| 1444314 | 4/1969 | Fed. Rep. of Germany . |
| 2725714 | 12/1977 | Fed. Rep. of Germany . |
| 2912485 | 10/1980 | Fed. Rep. of Germany . |
| 3327840 | 9/1984 | Fed. Rep. of Germany . |
| 3417912 | 7/1985 | Fed. Rep. of Germany . |
| 1125918 | 11/1956 | France . |
| 2162463 | 7/1973 | France . |
| 50-31193 | 3/1975 | Japan . |
| 52-038485 | 3/1977 | Japan . |
| 56-016405 | 2/1981 | Japan . |
| 56-022712 | 3/1981 | Japan . |
| 56-086113 | 7/1981 | Japan . |
| 56-129300 | 10/1981 | Japan . |
| 56-167799 | 12/1981 | Japan . |
| 57-050909 | 3/1982 | Japan . |
| 57-056413 | 4/1982 | Japan . |
| 57-064606 | 4/1982 | Japan . |
| 58-113300 | 7/1983 | Japan . |
| 58-177909 | 10/1983 | Japan . |
| 59-110612 | 6/1984 | Japan . |
| 60-126209 | 7/1985 | Japan . |
| 60-166400 | 8/1985 | Japan . |
| 849433 | 9/1960 | United Kingdom . |
| 964837 | 7/1964 | United Kingdom . |
| 992087 | 5/1965 | United Kingdom . |
| 1034782 | 7/1966 | United Kingdom . |
| 1191289 | 5/1970 | United Kingdom . |
| 1549180 | 7/1979 | United Kingdom . |
| 2039512 | 8/1980 | United Kingdom . |
| 2058103 | 4/1981 | United Kingdom . |
| 1598567 | 9/1981 | United Kingdom . |
| 1598845 | 9/1981 | United Kingdom . |
| 2074184 | 10/1981 | United Kingdom . |

OTHER PUBLICATIONS

Bennett, H., Editor, 1971, *Chemical Formulary*, vol. XVI, pp. 81, 82, 120.

*McCutcheon's Detergents and Emulsifiers*, North American Edition, 1978, pp. 238 and 240.

Bennett, H., Editor, 1973, *Chemical Formulary*, vol. XVII, p. 125.

Starch et al., "Silicones in Skin-Care Products", *Cosmetic Technology*, Nov., 1982, pp. 22-27.

Hunting, *Encyclopedia of Shampoo Ingredients*, Micelle Press, 1985, pp. 35, 50, 78, 95, 143, 204-205, 421.

Rothemann, Das Grosse Reseptbuch Der Haut-Und Korperpflegemittel, 1969, Dr. Alfred Huthig Verlag, Heidelberg, pp. 175, 247, 248, 608.

Merck Index, Tenth Edition, 1983, pp. 1258-1259.

Harry's Cosmeticology Treatise, 7th edition, 1982, pp. 446-457.

Liquid soap formulation (Dow Corning)—Product Description Sheet.

I Like My Gray shampoo (Clairol)—Product description, analysis and label.

deNavarre, Maison G., *The Chemistry and Manufacture of Cosmetics*, vol. IV, Second Edition, 1975, pp. 1297-1304.

Kirk-Othmer *Encyclopedia of Chemical Technology*, vol. 8, pp. 830, 831, 837.

*Ullmanns Encyclopedia*, 1976, Verlag Chemie, p. 542.

Janistyn Treatise, *Handbuch der Kosmetika und Riechstoffe*, Dr. Alfred Huthig Verlag, Heidelberg, 1978, p. 837.

Henkel Trade Leaflet, Mar., 1980—Coconut fatty acid monoethanolamide.

Jergens Lotion Enriched Soap—product description—from Cosmetic Research USA News, May, 1981.

IVORY Shampoo product label.

Hunting, Anthony L.L., Opacifiers and Pearling Agents in Shampoos, Cosmetics and Toiletries, vol. 96, pp. 65-78 (1981).

SHAMPOO COMPOSITIONS

Matter enclosed in heavy brackets [ ] appears in the original patent but forms no part of this reissue specification; matter printed in italics indicates the additions made by reissue.

CROSS REFERENCE TO RELATED APPLICATION

This is a continuation of application Ser. No. 795,285, filed on Nov. 5, 1985, now abandoned, which is a continuation-in-part of our copending application Ser. No. 670,189, filed Nov. 9, 1984, now abandoned.

TECHNICAL FIELD

The present invention is related to conditioning shampoos which have a dispersed, non-volatile silicone phase and are stabilized through the use of certain long chain materials.

BACKGROUND OF THE INVENTION

Human hair becomes soiled due to its contact with the surrounding atmosphere and, to a greater extent, from sebum secreted by the head. The build-up of the sebum causes the hair to have a dirty feel and an unattractive appearance. The soiling of the hair necessitates it being shampooed with frequent regularity.

Shampooing the hair cleans by removing excess soil and sebum. However, the shampooing process has disadvantages in that the hair is left in a wet, tangled and generally unmanageable state. A variety of approaches have been developed to alleviate the after-shampoo problems. These range from the inclusion of hair conditioning aids in shampoos to post-shampoo application of hair conditioners, i.e., hair rinses. Hair rinses typically work by depositing a polymeric film or other material onto the hair. However, such solutions to a very prevalent problem have not been fully satisfactory. For one thing, hair rinses are generally liquid in nature and must be applied in a separate step following the shampooing, left on the hair for a length of time, and rinsed with fresh water. This, of course, is time consuming and is not convenient.

While shampoos have been disclosed which contain conditioning aids, they have not been totally satisfactory for a variety of reasons. One problem relates to compatibility problems between good cleaning anionic surfactants and the fatty cationic agents which are good conditioning agents. This caused other surfactants such as nonionics, amphoterics and zwitterionics to be examined by workers in the field. Many of these efforts are reflected in patients issued in the conditioning shampoo are. See for example U.S. Pat. No. 3,849,348, Nov. 19, 1974 to Hewitt; U.S. Pat. No. 3,990,991, Nov. 9, 1961 to Gerstein; and U.S. Pat. No. 3,822,312, July 2, 1974 to Sato.

The use of these other surfactants solved many of the compatibility problems but still did not provide complete answers in all areas. For instance cationic conditioners may not deliver the desired level of softness desired by users. Materials which can provide increased softness are silicones, both those which are soluble as well as insoluble in the shampoo matrix.

Silicones in shampoo compositions have been disclosed in a number of different publications. Such publications include U.S. Pat. No. 2,826,551, Mar. 11, 1958 to Geen; U.S. Pat. No. 3,964,500, June 22, 1976 to Drakoff; U.S. Pat. No. 4,364,837, Dec. 21, 1982 to Pader; and British Pat. No. 849,433, Sept. 28, 1960 to Woolston. While these patents disclose silicone containing compositions, they also do not provide answers to all of the problems encountered in making a totally satisfactory product. One problem is that of keeping a dispersed, insoluble silicone material suspended and the total product stable. A variety of materials have been included in silicone containing shampoos for purposes of thickening and stabilization but totally satisfactory solutions are lacking. It has been surprisingly found that certain long chain acyl derivatives and certain other long chain derivatives can provide stabilization without interfering unduly with deposit of the silicone material onto the hair and other shampoo functions.

It is an object of the present invention to provide a stable silicone containing conditioning shampoo.

It is a further object of the present invention to provide silicone shampoo compositions containing certain long chain derivatives.

These and other objects will become readily apparent from the detailed description which follows.

Unless otherwise indicated, all percentages and ratios herein are by weight.

SUMMARY OF THE INVENTION

The present invention relates to shampoo compositions comprising from about 5% to about 70% of a synthetic surfactant, about 0.01% to about 10.0% of an insoluble, non-volatile silicone, about 0.5% to about 5.0% of a certain long chain derivative and water. These as well as optional components are described in detail below.

DETAILED DESCRIPTION

The essential components of the present invention are given in the following paragraphs.

Surfactant

An essential component of the present compositions is a surfactant. The surfactant, which may be selected from any of a wide variety of synthetic anionic, amphoteric, zwitterionic and nonionic surfactants, is present at a level of from about 5% to about 70%, preferably from about 10% to about 30%, most preferably from about 10% to about 22%.

Synthetic anionic surfactants can be exemplified by the alkali metal salts of organic sulfuric reaction products having in their molecular structure an alkyl radical containing from 8–22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and other known in the art.

Zwitterionic surfactants can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxyl, sulfonate, sulfate, phosphate, or phosphonate. A general formula for these compounds is:

$$R^2 \quad \overset{(R^3)_x}{Y^{(+)}} \quad CH_2 R^4 \quad Z^{(-)}$$

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:

4-[N,N-di(2-hydroxyethyl)-N-octadecylammonio]butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxypentane-1-sulfate.

Other zwitterionics such as betaines are also useful in the present invention. Examples of betaines useful herein include the high alkyl betaines such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxy-ethyl)carboxy methyl betaine, stearyl bis-(2-hydroxy-propyl)carboxymethyl betaine, oleyl dimethyl gamma-carboxypropyl betaine, lauryl bis-(2-hydroxypropyl)alpha-carboxyethyl betaine, etc. The sulfobetaines may be represented by coco dimethyl sulfopropyl betaine, stearyl dimethyl sulfopropyl betaine, lauryl dimethyl sulfoethyl betaine, lauryl bis-(2-hydroxy-ethyl)sulfopropyl betaine and the like; amido betaines and amidosulfobetaines, wherein the $RCONH(CH_2)_3$ radical is attached to the nitrogen atom of the betaine are also useful in this invention. The amido betaines are preferred for use in some of the compositions of this invention. A particularly preferred composition utilizes an amido betaine, a quaternary compound, a silicone, a suspending agent and has a pH of from about 2 to about 4.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

$$R_1R_2R_3N \quad O$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyl-dodecylamine oxide, oleyldi(2-hydroxyethyl)amine oxide, dimethyloctylamine oxide, dimethyl-decylamine oxide, dimethyltetradecylamine oxide, 3,6,9-trioxaheptadecyldiethylamine oxide, di(2-hydroxyethyl)-tetradecylamine oxide, 2-dode-coxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

RR'R''P O wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9,-trioxaoctadecyldimethylphosphine oxide, cetyldimethylphosphine oxide, 3-dodecoxy-2-hydroxypropyldi(2-hydroxyethyl)phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9,-trioxaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Many additional nonsoap surfactants are described in McCUTCHEON'S, DETERGENTS AND EMULSIFIERS, 1979 ANNUAL, published by Allured Publishing Corporation, which is incorporated herein by reference.

The above-mentioned surfactants can be used alone or in combination in the shampoo compositions of the present invention. The anionic surfactants, particularly the alkyl sulfates, the ethoxylated alkyl sulfates and mixtures thereof are preferred for use herein as well as the amido betaines.

Non-Volatile Silicone Fluid

Silicone fluids are a suitable non-volatile silicone that may be used in the present compositions.

The non-volatile silicone fluid may be either a polyalkyl siloxane, a polyaryl siloxane, a polyalkylaryl siloxane or a polyether siloxane copolymer and is present at a level of from about 0.1% to about 10.00% preferably from about 0.5% to about 5.0%. Mixtures of these fluids may also be used and are preferred in certain executions. The dispersed silicone particles should also be insoluble in the shampoo matrix. This is the meaning of "insoluble" as used hereinbefore and hereinafter.

The essentially non-volatile polyalkyl siloxane fluids that may be used include, for example, polydimethyl siloxanes with viscosities ranging from about 5 to 600,000 centistokes at 25° C. These siloxanes are available, for example, from the General Electric Company as the Viscasil series and from Dow Corning as the Dow Corning 200 series. The viscosity can be measured by means of a glass capillary viscometer as set forth in Dow Corning Corporate Test Method CTM0004, July 20, 1970. Preferably the viscosity ranges from about 350 centistokes to about 100,000 centistokes.

The essentially non-volatile polyalkylaryl siloxane fluids that may be used include, for example, polymethylphenylsiloxanes having viscosities of about 15 to 30,000 centistokes at 25° C. These siloxanes are available, for example, from the General Electric Company as SF 1075 methyl phenyl fluid or from Dow Corning as 556 Cosmetic Grade Fluid.

The essentially non-volatile polyether sioxane copolymer that may be used is, for example, a polypropylene oxide modified dimethylpolysiloxane (e.g., Dow Corning DC-1248) although ethylene oxide or mixtures of ethylene oxide and propylene oxide may also be used.

References disclosing suitable silicone fluids include the previously mentioned U.S. Pat. No. 2,826,551 to Geen; U.S. Pat. No. 3,964,500, June 22, 1976 to Drakoff; U.S. Pat. No. 4,364,837 to Pader and British Pat. No. 849,433 to Woolston. All of these patents are incorporated herein by reference. Also incorporated herein by reference is Silicon Compounds distributed by Petrarch Systems, Inc., 1984. This reference provides a very good listing of suitable silicone materials.

Another silicone material found especially useful in the present compositions to provide good dry combing is a silicone gum. Silicone gums described by Petrarch and others including U.S. Pat. No. 4,152,416, May 1, 1979 to Spitzer, et al. and Noll, Walter, Chemistry and Technology of Silicones, New York: Academic Press 1968. Also describing silicone gums are General Electric Silicone Rubber Product Data Sheets SE 30, SE 33, SE 54 and SE 76. All of these described references are incorporated herein by reference. "Silicone gum" materials denote high molecular weight polydiorganosiloxanes having a mass molecular weight of from about 200,000 to about 1,000,000. Specific examples include polydimethylsiloxane, (polydimethylsiloxane) (methylvinylsiloxane) copolymer, poly(dimethylsiloxane) (diphenyl) (methylvinylsiloxane) copolymer and mixtures thereof.

Long Chain Derivative Suspending Agent

The suspending agent useful in the present compositions can be any of several long chain acyl derivative materials or mixtures of such materials. Included are ethylene glycol esters of fatty acids having from about 16 to about 22 carbon atoms. Preferred are the ethylene glycol stearates, both mono and distearate, but particularly the distearate containing less than about 7% of the mono stearate. Other suspending agents found useful are alkanol amides of fatty acids, having from about 16 to about 22 carbon atoms, preferably from 16 to 18 carbon atoms. Preferred alkanol amides are stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide DEA distearate, stearamide MEA stearate).

Still other suitable suspending agents are alkyl ($C_{16-22}$) dimethyl amide oxides such as stearyl dimethyl amine oxide. If the compositions contain an amide oxide or a long chain acyl derivative as a surfactant the suspending function could also be provided and additional suspending agent may not be needed if the level of those materials are at least the minimum level given below.

The suspending agent is present at a level of from about 0.50% to about 5.0%, preferably from about 0.5% to about 3.0%. The suspending agent serves to assist in suspending the silicone material and may give pearlescence to the product. Mixtures of suspending agents are also suitable for use in the compositions of this invention.

Water

Water is the last essential component of the present invention and forms the remainder of the composition. It is generally present at a level of from about 20% to about 95%, preferably from about 60% to about 85%.

Optional Components

The shampoos herein can contain a variety of non-essential optional components suitable for rendering such compositions more acceptable. Such conventional optional ingredients are well known to those skilled in the art, e.g. preservatives such as benzyl alcohol, methyl paraben, propyl paraben and imidazolidinyl urea; cationic surfactants such as cetyl trimethyl ammonium chloride, lauryl trimethyl ammonium chloride, tricetyl methyl ammonium chloride, stearyldimethyl benzyl ammonium chloride, and di(partially hydrogenated tallow)dimethylammonium chloride; thickeners and viscosity modifiers such as a diethanolamide of a long chain fatty acid (e.g., PEG 3lauramide), block polymers of ethylene oxide and propylene oxide such as Pluronic F88 offered by BASF Wyandotte, sodium chloride, sodium sulfate, polyvinyl alcohol, and ethyl alcohol; pH adjusting agents such as citric acid, succinic acid, phosphoric acid, sodium hydroxide, sodium carbonate, etc.; perfumes; dyes; and, sequestering agents such as disodium ethylenediamine tetraacetate. Such agents generally are used individually at a level of from about 0.01% to about 10%, preferably from about 0.5% to about 5.0% by weight of the composition.

The pH of the present compositions is not critical and may be in the range of from about 2 to about 10. However, as set forth earlier certain zwitterionic/quaternary compositions preferably have pH's of from about 2 to about 4.

METHOD OF MANUFACTURE

The shampoos of the present invention can be made by mixing the materials together and heating to about 72° C. The mixture is mixed thoroughly for about 10 minutes at the 72° C. temperature before being pumped through a high shear mill and then through a heat exchanger to cool it to about 27° C.

The high shear mill is used to achieve adequate dispersion of the silicone fluid. This is achieved by having the average particle size of the silicones preferably to about 10 microns or less.

In the cooling step, the acyl derivative is preferably crystallized into particles having an average particle size of about 10 microns or less.

INDUSTRIAL APPLICABILITY

The present compositions are used in a conventional manner for cleaning hair. From about 0.1 g to about 10 g of a composition is applied to hair that has been wetted, generally with water, worked through the hair and then rinsed out.

The following Examples further describe and demonstrate the preferred embodiments within the scope of the present invention. The Examples are given solely for the purpose of illustration and are not to be construed as limitations of the present invention as many variations thereof are possible without departing from its spirit and scope.

EXAMPLES I-V

The following compositions are representative of the present invention.

| | Weight % | | | | |
|---|---|---|---|---|---|
| Component | I | II | III | IV | V |
| Cocamidopropyl | 18.00 | 18.00 | 18.00 | 18.00 | 18.00 |
| Betaine | 4.00 | 2.00 | 2.00 | 2.00 | 2.00 |
| Di-partially hydrogenated tallow dimethyl ammonium chloride | | | | | |
| Cetyltrimethylammonium chloride | 2.00 | 2.00 | 2.00 | 2.00 | 2.00 |
| DC-200 Fluid (350 csk)[1] | — | 1.00 | — | 1.75 | — |
| DC-200 Fluid (12500 csk)[2] | 1.00 | — | — | — | — |
| DC-1248[3] | — | — | 1.00 | — | — |
| DC-X28107 | — | — | — | — | 1.00 |
| Citric Acid | 3.50 | 3.50 | 3.50 | 3.50 | 3.50 |
| Ethylene Glycol Distearate | 1.50 | 1.50 | 1.50 | 1.50 | 1.50 |
| PEG-3 Alkyl amide[4] | 3.00 | 4.50 | 4.50 | 4.50 | 4.50 |
| Sodium Chloride | — | — | 1.00 | — | — |
| Preservative, Dye, | | | qs 100.00% | | |
| Perfume and Water | — | — | — | — | — |
| pH | 3.0 | 3.0 | 3.0 | 3.0 | 3.0 |

[1]Dimethylpolysiloxane offered by Dow Chemical Co.
[2]Dimethylpolysiloxane offered by Dow Chemical Co.
[3]A dimethicone offered by Dow Chemical Co.
[4]PEG-3 Allyl (98% $C_{12}$) Amide - Mazamide C-2 Experimental These compositions are stable and deliver good conditioning to hair that is washed with the compositions.

EXAMPLES VI & VII

The following are two anionic shampoo compositions of the present invention.

| | Weight % | |
|---|---|---|
| Component | VI | VII |
| TEA $C_{12}$–$C_{14}$ Alkyl Sulfate | 15.00 | — |

-continued

| Component | Weight % VI | Weight % VII |
|---|---|---|
| $NH_4$ $C_{12}$–$C_{14}$ Alkyl (Ethoxy)$_3$ Sulfate | — | 7.90 |
| Sodium $C_{12}C_{14}$ Alkyl Sulfate | — | 7.90 |
| Cocamide MEA | 3.00 | 1.50 |
| Dimethicone DC-200[1] | 3.00 | 3.00 |
| Ethylene Glycol Distearate | 1.50 | 1.50 |
| Citric Acid | 0.60 | 0.60 |
| Trisodium Citrate | 0.30 | — |
| Q.S. Color, Preservative, Perfume and Water | *q.s. 100%* | *q.s. 100%* |

[1]Polydimethylsiloxane having a viscosity of 12,500 centistokes

These compositions are also stable and deliver good hair conditioning.

EXAMPLE VIII

To demonstrate the benefit given by the ethylene glycol distearate to the present compositions, the compositions of Examples I–V are prepared without the material. When samples were stored at 50° F., 80° F. and 100° F., all of the compositions without EGDS demonstrated instability with the silicone rising to the top in a clear layer. None of the compositions of the present invention demonstrated any instability. This clearly demonstrates the superiority of the present invention.

What is claimed is:

1. A shampoo composition comprising (a) from about 5% to about 70% of a synthetic surfactant selected from the group consisting of anionic surfactants, zwitterionic surfactants, amphoteric surfactants and mixtures thereof;

(b) from about 0.01% to about 10% of a dispersed, insoluble, nonvolatile silicone *in the form of fluids or gums selected from the group consisting of polyalkyl siloxanes, polyaryl siloxanes, polyalkylaryl siloxanes, polyether siloxane copolymers, and mixtures thereof;*

(c) from about 0.5% to about 5% of a long chain ($C_{16}$–$C_{22}$) acyl derivative or long chain ($C_{16}$–$C_{22}$) amine oxide *suspending agent* selected from the group consisting of ethylene glycol long chain esters, alkanol amides of long chain fatty acids, long chain esters of long chain fatty acids, glyceryl long chain esters, long chain esters of long chain alkanolamides, long chain alkyl dimethyl amine oxides and mixtures thereof; and (d) the remainder water.

2. A shampoo composition according to claim 1 wherein the non-volatile silicone is selected from the group consisting of polydimethylsiloxanes having viscosities of from about 5 to about 100,000 centistokes at 25° C., polypropylene oxide modified dimethylsiloxanes and silicone gums.

3. A shampoo composition according to claim 2 wherein the surfactant is selected from the group consisting of amphoteric surfactants, zwitterionic surfactants and mixtures thereof.

4. A shampoo composition according to claim 2 wherein the surfactant is anionic.

5. A shampoo composition according to claim 3 wherein the non-volatile silicone is selected from the group consisting of polydimethylsiloxanes having viscosities of from about 5 to about 100,000 centistokes at 25° C. and polypropylene oxide modified dimethylsiloxanes.

6. A shampoo composition according to claim 5 which in addition contains from about 0.01% to about 10% of a quaternary ammonium compound.

7. A shampoo composition according to claim 6 wherein the surfactant is a betaine.

8. A shampoo composition according to claim 7 wherein the acyl derivative is ethylene glycol distearate.

9. A shampoo composition according to claim 8 wherein the shampoo composition has a pH of from about 2 to about 4.

*10. A shampoo composition comprising*

*(a) from about 5% to about 70% of a synthetic surfactant selected from the group consisting of anionic surfactants, zwitterionic surfactants, amphoteric surfactants, and mixtures thereof;*

*(b) from about 0.01% to about 10% of a dispersed, insoluble, non-volatile silicone in the form of fluids or gums selected from the group consisting of polyalkyl siloxanes, polyaryl siloxanes, polyalkylaryl siloxanes, polyether siloxane copolymers, and mixture thereof;*

*(c) from about 0.5% to about 5% of a long chain ($C_{16}$–$C_{22}$) acyl derivative suspending agent selected from the group consisting of long chain ($C_{16}$–$C_{22}$) esters, long chain ($C_{16}$–$C_{22}$) ethanol amides, and mixtures thereof, said suspending agent being present in the shampoo composition in crystalline form; and*

*(d) the remainder water.*

*11. A shampoo composition according to claim 10 wherein the crystals of the suspending agent in the shampoo composition have an average particle size of about 10 microns or less.*

*12. A shampoo composition according to claim 11 wherein the non-volatile silicone is selected from the group consisting of polydimethylsiloxanes having viscosities of from about 5 to about 100,000 centistokes at 25° C., polypropylene oxide modified dimethylsiloxanes, and silicone gums, and mixtures thereof.*

*13. A shampoo composition according to claim 12 wherein the non-volatile silicone is selected from the group consisting of polydimethylsiloxanes having viscosities of from about 5 to about 100,000 centistokes at 25° C., polypropylene oxide modified dimethylsiloxanes, and mixtures thereof.*

*14. A shampoo composition according to claim 12 wherein the surfactant is anionic.*

*15. A shampoo composition according to claim 12 wherein the surfactant is selected from the group consisting of amphoteric surfactants, zwitterionic surfactants, and mixtures thereof.*

*16. A shampoo composition according to claim 15 wherein the surfactant is a betaine.*

*17. A shampoo composition according to claim 14 wherein the acyl derivative is ethylene glycol distearate.*

*18. A shampoo composition according to claim 14 which in addition contains from about 0.01% to about 10% of a quaternary ammonium compound.*

*19. A shampoo composition according to claim 14 having a pH of from about 2 to about 4.*

*20. A shampoo composition according to claim 10 wherein the silicone has an average particle size of about 10 microns or less.*

* * * * *

UNITED STATES PATENT AND TRADEMARK OFFICE

CERTIFICATE OF CORRECTION

PATENT NO. : Re. 34,584

DATED : April 12, 1994

INVENTOR(S) : Mark B. Grote and Glen D. Russell

It is certified that error appears in the above-identified patent and that said Letters Patent is hereby corrected as shown below:

Column 10, line 27, should read "esters, long chain ($C_{16}$-$C_{22}$) alkanol amides, and".

Signed and Sealed this

Thirty-first Day of January, 1995

*Attest:*

Bruce Lehman

BRUCE LEHMAN

*Attesting Officer*

*Commissioner of Patents and Trademarks*